(12) United States Patent
Mamidi et al.

(10) Patent No.: US 6,504,012 B2
(45) Date of Patent: *Jan. 7, 2003

(54) METHOD FOR PREPARING DUAL VIRALLY INACTIVATED IMMUNE GLOBULIN FOR INTRAVENOUS ADMINISTRATION

(75) Inventors: Raja R. Mamidi, Pomona, CA (US); Andranik Bagdasarian, San Dimas, CA (US); Gorgonio Canaveral, Walnut, CA (US); Kazuo Takechi, Osaka (JP)

(73) Assignee: Alpha Therapeutic Corporation, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/861,713

(22) Filed: May 22, 2001

(65) Prior Publication Data

US 2001/0044524 A1 Nov. 22, 2001

Related U.S. Application Data

(63) Continuation of application No. 09/316,117, filed on May 20, 1999.

(51) Int. Cl.[7] .................. A61K 35/16; C07K 16/00
(52) U.S. Cl. .............. 530/386; 530/380; 530/383; 530/384; 530/390.1; 530/390.5
(58) Field of Search ................. 530/380, 383, 530/384, 386, 390.1, 390.5

(56) References Cited

U.S. PATENT DOCUMENTS

| | | | |
|---|---|---|---|
| 4,216,205 A | 8/1980 | Radowitz | |
| 4,820,805 A | 4/1989 | Neurath et al. | |
| 4,835,257 A | 5/1989 | Friedrich-Fiechtl et al. | |
| 4,841,023 A | 6/1989 | Horowitz | |
| 4,845,199 A | 7/1989 | Hirao et al. | |
| 4,874,708 A | 10/1989 | Makula et al. | |
| 5,110,910 A | 5/1992 | Tsav | |
| 5,132,406 A | 7/1992 | Uemura et al. | |
| 5,151,499 A | 9/1992 | Kameyama et al. | |
| 5,177,194 A | 1/1993 | Sarno et al. | |
| 5,190,752 A | 3/1993 | Möller et al. | |
| 5,300,433 A | 4/1994 | Hrinda et al. | |
| 5,371,196 A | 12/1994 | Yuki et al. | |

OTHER PUBLICATIONS

Uemura et al., Vox Sang 56:155–161, 1989.*

* cited by examiner

*Primary Examiner*—Brenda Brumback
(74) *Attorney, Agent, or Firm*—Sughrue Mion, PLLC

(57) ABSTRACT

A process for producing an intravenously-administrable gamma globulin solution substantially free of contaminating viruses by fractionating an impure gamma globulin solution and then treating the purified gamma globulin, in any order, with a solvent-detergent for viral inactivation and a heat treating for viral inactivation. Thereafter, denatured impurities, residual solvent and aggregate generated by the heat treatment are removed from the gamma globulin.

2 Claims, No Drawings

US 6,504,012 B2

METHOD FOR PREPARING DUAL VIRALLY INACTIVATED IMMUNE GLOBULIN FOR INTRAVENOUS ADMINISTRATION

This application is a Continuation Application of U.S. application Ser. No. 09/316,117 filed May 20, 1999, the disclosure of which is incorporated herein by reference.

BACKGROUND OF THE INVENTION

The present invention relates to an integral, multi-step commercial process for the production of intravenously administrable immune globulin containing IgG (γ-globulin) as the main ingredient.

Various processes are known for obtaining intravenously administrable γ-globulin solutions from starting materials resulting from Cohn fractionation of human plasma. Certain of the Cohn fractions contain higher titres of γ-globulin than others. Usual starting materials for a γ-globulin solution are Cohn Fraction II or Cohn Fraction II+III.

Although prior art processors employ various separation and sterilization techniques, process modifications are constantly sought for improving final product purity and safety, and overall yield.

Many commercial processes employ either a solvent/detergent step for viral inactivation, or a heat treatment step for viral inactivation. To date, the art has not provided a multi-step process beginning with Cohn Fraction II paste or II+III paste including two different viral inactivation procedures as part of an efficient, high yield γ-globulin manufacturing process.

U.S. Pat. No. 5,151,499 by Kameyama et al. is directed to a process for producing viral inactivated protein compositions in which a protein composition is subjected to a viral inactivation for envelope viruses in a solvent/detergent treatment of the protein composition and a viral inactivation for non-envelope viruses in a heat treatment of the protein composition. The '499 patent teaches that preferably the solvent/detergent step occurs first and in the presence of a protease inhibitor, followed by a heat treatment, which in most examples thereof is a dry heat treatment. Where the heat treatment is carried out in the liquid state, the protein is first recovered from the solvent/detergent by adsorption onto an ionic exchange column, prior to any heat treatment. The liquid heat treatment can be carried out in the presence of a sugar, sugar alcohol or amino acid stabilizer. Although the '499 patent lists many starting protein compositions including immunoglobulin, its production examples employ Factor VIII, Factor IX, thrombin, fibrinogen and fibronectin.

U.S. Pat. No. 5,371,196 by Uuki et al. is directed to purifying secretory immunoglobulin A. A liquid heat treatment or various combinations of liquid heat treatment and solvent treatment viral inactivation are described. A polyethylene glycol fractionation is employed following each step and always as a final step. This patent does not relate to immune serum globulin of high γ-globulin titre.

Certain prior art processes for production of intravenously injectable γ-globulin solutions describe the incorporation of a liquid heat treatment carried out in the presence of sorbitol heat stabilizer in a multi-step purification procedure beginning with Cohn Fraction II+III paste. In U.S. Pat. No. 4,845,199 by Hirao et al., Cohn Fraction II+III is subjected to polyethylene glycol (hereinafter "PEG") fractionation (8% w/v PEG for precipitating impurities and aggregate followed by 12% w/v PEG for precipitating the γ-globulin), then ion exchange chromatography (DEAE-Sephadex®, Pharmacia, anion exchanger and removal of human blood group antibody prior to a liquid heat treatment in the presence of sorbitol as a protein stabilizer. On the other hand, Example 1 of U.S. Pat. No. 4,876,088 by Hirao et al. describes the preparation of intravenously injectable γ-globulin solution from Cohn Fraction II+III paste in which the paste is suspended in water, its pH adjusted to 5.5 and centrifuged, with the supernatant then being heat treated for viral inactivation in the presence of 33% w/v of sorbitol, followed by PEG fractionation (6%/12%), and then by other purification steps including DEAE-Sephadex ion exchange chromatography.

SUMMARY OF THE INVENTION

An object of the present invention is to provide an integral, commercially useable process for producing a highly purified γ-globulin solution from the Cohn fractionation process.

Another object of the present invention is to provide very pure intravenously administrable γ-globulin solution free of both envelope and non-envelope viruses, including all heat sensitive viruses.

A further object of the present invention is to provide a commercial γ-globulin process including two sequential viral inactivation steps without the need for recovery of γ-globulin protein following the first viral inactivation step nor prior to the second viral inactivation step.

The above and other objects which will be apparent to the skilled artisan are provided by the present invention in which an alcoholic Cohn fraction, which may be partially purified, but is rich in γ-globulin, is first subjected to PEG fractionation, and then to two viral inactivation treatments, one being a viral inactivation in the presence of a solvent, preferably a solvent-detergent mixture, for disruption of envelope viruses, and the other being a heat treatment viral inactivation, without recovery of γ-globulin between the two viral inactivations. Then, any aggregate formed by the heat treatment is removed from the heat treated and solvent treated solution.

In a preferred embodiment of the present invention, sorbitol is the heat stabilizer and trialkyl phosphate is the solvent.

In another embodiment of the present invention, any particulates present are removed prior to the solvent-detergent treatment.

In another embodiment of the present invention, the γ-globulin solution is subjected to PEG fractionation following the completion of viral inactivation.

In yet another embodiment of the present invention, the γ-globulin solution is treated with a cationic exchange resin following the completion of viral inactivation.

In certain preferred embodiments of the present invention a single stage polyethylene glycol fractionation step is carried out without precipitation of the γ-globulin.

In another preferred embodiment of the invention, solvent-detergent viral inactivation is carried out before the heat treatment viral inactivation.

In still another embodiment of the invention, there is provided a heat-sterilized and solvent-detergent sterilized γ-globulin suitable for intravenous administration.

DETAILED DESCRIPTION OF THE INVENTION

A fraction containing immunoglobulin is used as the staring material. This fraction is not particularly limited in so far as it originates from human plasma and contains an immunoglobulin fraction. Specific examples of such an immunoglobulin-containing fraction include Fraction II+III and Fraction II obtainable by ethanol fractionation of Cohn, and paste of immunoglobulin-containing fractions equivalent thereto. Other starting materials are Fractions I+II+III, and Fraction II+IIIw. The starting material may contain impurities, such as human blood-group antibodies, plasminogen, plasmin, kallikrein, prekallikrein activator, IgM, IgA, IgG polymers (hereinafter and hereinbefore "aggregates"), etc.

The preferred starting materials are Cohn Fraction II or Cohn Fraction II+III. When Cohn Fraction II+III paste is used, it is recommended that it first be subjected to a preliminary washing procedure to form Fraction II+IIIw, which is thereafter used in the process of this invention. "Fraction II+IIIw" is a disodium phosphate solution-washed Cohn Fraction II+III precipitate.

Fraction II+IIIw can be obtained by suspending Fraction II+III precipitate in cold water for injection in a ratio of about 1 kilogram of II+III paste per about 20 volumes of water. A sodium phosphate solution is added to the final concentration of approximately 0.003M sodium phosphate for solubilizing lipids, lipoproteins and albumin. Cold ethanol is added to bring the final alcohol concentration to about 20%. During the alcohol addition, temperature is gradually lowered to −5±1° C. and pH is maintained or adjusted to 7.2±0.1, for example by using acetate buffer or dilute sodium hydroxide. The Fraction II+IIIw precipitate which forms is recovered by centrifugation and/or filtration while maintaining the temperature at −5±1° C.

Prior to PEG fractionation as carried out in accordance with the processing sequence of the present invention, various preliminary purification and/or aggregate-reducing steps can be carried out. For example, when Fraction II+III paste is used, typically containing about 20% alcohol, and more than 70% of the protein present is IgG, the Fraction II+IIIw paste can be suspended in 3 to 10 volumes, preferably 3 to 5 volumes, of cold water at a temperature of about 0 to 5° C. and with pH being adjusted to be between 4.5 to 6.0, preferably 5.0 to 5.5 using pH 4.0 acetate buffer or hydrochloric acid. The mixture is agitated for about 2 to 15 hours to allow all of the γ-globulin to go into solution. Thereafter, undissolved protein such as albumin and α-globulins can be removed by centrifugation and/or filtration.

Where a different starting Cohn fraction is employed, the initial step or steps of the process can be appropriately selected where desired for carrying out a preliminary purification for obtaining a fraction of high IgG content to be further processed. For example, where Cohn Fraction II (contains over 95% pure IgG) has been separated from Cohn Fraction III, with Fraction II to be further processed, the initial processing can be at an acid pH of 3.2 to 5.0, preferably 3.8 to 4.2, as described by Uemura et al. U.S. Pat. No. 4,371,520, in order to break down immune globulin aggregates present into immune globulin monomers and dimers, since aggregates are known to possess anti-complementary activity (ACA). As another alternative, with Cohn Fraction II+III starting material, the Uemura, et al. patent low pH treatment can be carried out as an additional step following an initial purification step as above described and prior to the PEG fractionation step.

PEG fractionation is carried out prior to the viral inactivation. PEG fractionation is a well known procedure in the art of purification of immune globulin in order to separate the desired IgG monomer and dimer from IgG aggregate and from other impurities naturally occurring in the starting plasma protein fraction. The removal of aggregate and some of the impurities present prior to the viral inactivation reduces the degree of aggregation and turbidity otherwise occurring during the heat treatment step, for example, when carried out at 60° C. for 10 hours.

A second PEG fractionation step following heat treatment viral inactivation is beneficial in removing denatured impurities and/or aggregates generated during the heat treatment process.

Any of the PEG fractionation procedures documented in the prior art can be used. In general, one stage or two stages of PEG fractionation are carried out. In the first stage of PEG fractionation, PEG concentration and pH are selected so that the desired IgG monomer and dimer remain in solution while undesired proteins such as aggregate are precipitated out of solution. Following centrifugation and/or filtration, PEG concentration is optionally increased with adjusting the pH to cause the desired IgG monomer and dimer to precipitate.

For example, a first stage of PEG fractionation can be carried out at a pH of about 5.0 to 7.5, preferably within about 6.5 to 7.5 pH when Fraction II+IIIw paste is used as starting material, and preferably within about 5.5 to 6.0 pH when Fraction II+III paste is used as starting material, with a PEG concentration ranging from about 4 to 8%, preferably either 4 to 6% when Fraction II+IIIw paste is used as starting material, or 6 to 8% when Fraction II+III paste is used as starting material. While maintaining cold temperatures of about 0 to 2° C., the first stage of PEG fractionation can be carried out for about 1 to 8 hours, after which the precipitate containing undesired protein including aggregate is removed as above-described. Where it is desired to collect the purified immunoglobulin, the filtrate will then have its pH adjusted to about 8.0 to 9.0, preferably about 8.5 to 8.9, and additional PEG added for final concentration of about 10 to 15%, preferably about 12%. The precipitate formed, which is purified immunoglobulin, is removed by filtration and/or centrifugation.

Further details of PEG fractionation procedures usable in the practice of the present invention can be found in the above-described U.S. Pat. No. 4,876,088 by Hirao et al. and U.S. Pat. No. 4,845,199 by Hirao et al.

The next essential step of the present invention is to carry out a first viral inactivation procedure selected from a heat treatment and a solvent or solvent-detergent mixture treatment. Therefore, a second viral inactivation procedure, which is the other of the heat treatment and solvent or solvent-detergent treatment not used as the first viral inactivation, is carried out. As described below, further purification procedures, specifically those involving the use of ionic exchange resins, can be carried out prior to and/or following the solvent-detergent treatment and/or following the heat treatment.

A particularly advantageous procedure is to carry out an anionic exchange treatment prior to the solvent detergent viral inactivation as a first viral inactivation and then a cationic exchange treatment after the heat treatment viral inactivation as a second viral inactivation. By this procedure, certain undesirable protein materials (such as prekallikrein activator, IgA, IgM and albumin) found within human plasma can be removed from the IgG by use of the anionic exchanger and then further such materials (prekallikrein activator, IgA, IgM and albumin) along with the PEG, residual reagents from the solvent-detergent treatment and denatured proteins (impurities and/or aggregates) resulting from the heat treatment can be removed through the cationic exchange procedure. Thus, the cationic exchange procedure can be employed in place of the second PEG fractionation after completion of viral inactivation for removing the denatured impurities and aggregate generated by the heat treatment viral inactivation.

If not otherwise accomplished during the overall process, the solution to be subjected to the solvent-detergent should be treated for removal of all particulate matter, which can include denatured protein. Therefore, it is preferred to filter the solution with a 1 micron or finer filter prior to solvent-detergent addition. This will also reduce the likelihood of virus being present within a large particle and thereby possibly avoiding exposure to the solvent-detergent.

Today, the preferred solvent for inactivation of envelope viruses is trialkyl phosphate. The trialkyl phosphate used in the present invention is not subject to particular limitation, but it is preferable to use tri(n-butyl)phosphate (hereinafter "TNBP"). Other usable trialkyl phosphates are the tri(ter-butyl)phosphate, the tri(n-hexyl)phosphate, the tri(2-ethylhexyl)phosphate, and so on. It is possible to use a mixture of 2 or more different trialkyl phosphates.

The trialkyl phosphate is used in an amount of between 0.01 to 10 (w/v) %, preferably about 0.1 to 3 (w/v) %.

The trialkyl phosphate may be used in the presence or absence of a detergent or surfactant. It is preferable to use trialkyl phosphate in combination with the detergent. The detergent functions to enhance the contact of the viruses in the immune globulin composition with the trialkyl phosphate.

Examples of the detergent include polyoxyethylene derivatives of a fatty acid, partial esters of anhydrous sorbitol such as Polysorbate 80 (Tradename: Tween 80, etc.) and Polysorbate 20 (Tradename: Tween 20, etc.); and non-ionic oil bath rinsing agent such as oxyethylated alkylphenol (Tradename: Triton X100, etc.) Examples include other surfactants and detergents such as Zwitter ionic detergents and so on.

When using the detergent, it is not added in a critical amount; for example, it may be used at ratios between about 0.001% and about 10%, preferably between about 0.01% and 3%.

In the present invention, the trialkyl phosphate treatment of the immune globulin containing composition is carried out at about 20 to 35° C., preferably 25 to 30° C., for more than 1 hour, preferably about 5 to 8 hours, more preferably about 6 to 7 hours.

During the trialkyl phosphate treatment, immune globulin is present at about a 3 to 8% protein solution in aqueous medium.

The trialkyl phosphate and optional detergent can be added directly to the filtrate resulting from a single stage of PEG fractionation where the γ-globulin is not to be precipitated by adding additional PEG. Dilution of the protein may be necessary. Otherwise, the precipitated γ-globulin is suspended in cold water for injection, pH can be adjusted to about 5.0 to 6.0, and the organic solvent and optional detergent are added thereto.

For the heat sterilization step, the solution of the immune globulin protein as obtained from the PEG fractionaction or from the solvent (detergent) step without purification is used as is, and a sugar, sugar alcohol and/or amino acid heat stabilizer is added thereto. pH is adjusted to about 4.5 to 6.0; preferably about pH 5.0 to 5.5. The heat stabilizer is preferably sucrose, maltose, sorbitol or mannitol, most preferably sorbitol. The sugar or sugar alcohol is added to the immune globulin solution as a powder or first mixed with a small volume of water and then added, to provide a final concentration of about 10 to 50 w/w %, up to saturation.

Following addition of the heat stabilizer, the mixture is heated at about 50–70° C. for about 10–100 hours, preferably at about 60° C., for about 10 to 20 hours, for viral inactivation of heat sensitive viruses. The heat treatment step not only inactivates viruses, but also through the protein denaturization effect thereof, can preferentially reduce the amount of cerin undesirable proteins normally associated with Cohn Fractions II+III, such as prekallikrein activator, plasmin and plasminogen.

After the heat treatment, the solution is cooled to about 0 to 30° C., preferably about 10° C. and pH is adjusted to about 5.0 to 6.0, preferably about pH 5.0 to 5.5.

If not carried out prior to the solvent-detergent treatment, an anionic exchange treatment can be carried out on the heat treated immune globulin. Preferably, at least a cationic exchange treatment is carried out on the heat treated product after completion of viral inactivation and the anionic exchange treatment is carried out prior to use of the solvent-detergent treatment as a first viral inactivation. The ionic exchange treatments are carried out with immune globulin dissolved in an aqueous solvent, generally having a pH of about 5.0 to 5.5, with where desired low ionic strength for maximum adsorption of IgG. The protein concentration generally is within the range of about 1–15 w/v %, more preferably from about 3 to 10 w/v %. The ionic exchanger is equilibrated with the same aqueous solvent as used, and either a batch or continuous system can be carried out. For instance, anionic exchange batch-wise treatment can be carried out by mixing the immune globulin solution with the anionic exchanger in an amount from about 10 to 100 ml per ml of the pretreated anionic exchanger (for example, 1 gram of DEAE Sephadex A-50 resin swells to about 20 grams wet weight in 0.4% sodium chloride solution), stirring the mixture at about 0–5° C. for about 0.5 to 5 hours, and then filtering or centrifuging at 6,000 to 8,000 rpm for 10 to 30 minutes to recover the supernatant liquor. Continuous treatment can be affected by passing immune globulin solution through a column of the anionic exchanger at a flow rate sufficient to adsorb impurities to the ionic exchanger and recovering the non-adsorbed fraction.

The anionic exchanger to be used, for example, comprises anion exchanging groups bonded to an insoluble carrier. The anion exchanging groups include diethylaminoethyl (DEAE), a quaternary aminoethyl (QAE) group, etc., and the insoluble carrier includes agarose, cellulose, dextran, polyacrylamide, etc.

Examples of usable cationic exchangers are carboxy methyl Sephadex (CM-Sephadex®, Pharmacia) CM-cellulose, SP-Sephadex®, Pharmacia), CM-Sepharose and SP-Sepharose. 1 ml of pretreated cationic exchanger (for example, 1 gram of CM-Sephadex®, Pharmacia) C-50 resin swells to about 30–35 grams wet weight in 0.4% sodium chloride solution) is mixed with 0.5 ml to 5 ml of immune globulin solution and stirred at 0–5° C. for 1–6 hours. The suspension is centrifuged or filtered to recover the IgG adsorbed resin. Also, a continuous process can be employed.

When the above-described conditions are used with the cationic exchanger, the IgG will be adsorbed, and thereafter following washing of the protein-adsorbed cationic exchange resin, IgG can be eluted, for example by about a 1.4 N sodium chloride solution.

Following the steps of the above process, the IgG is clarified, diafiltered and concentrated to the extent needed. If desired, a stabilizer such as D-sorbitol can be added and final adjustments made to yield a solution of a composition containing about 50 mg/ml or 100 mg/ml IgG, and 50 mg/ml D-sorbitol, with pH being at 5.4. This solution is then sterile filtered through sterilized bacterial retentive filters and filled into vials.

The following example is set forth to illustrate the invention but is nonlimiting. limiting.

Where desired, other immune globulin purification procedures can be appropriately combined with the processes described herein. For example, a bentonite clarification step, useful for reducing the levels of kallikrein and pre-kallikrein activator can be employed. An illustration of this is set forth in Example 1, hereinbelow.

EXAMPLE 1
Solvent-detergent and Heat Treated γ-Globulin

Six hundred and eighty five grams of Fr II+IIIw paste is suspended in about 11.9 kg of cold water. Sodium acetate trihydrate solution is added to the suspension to a final concentration of approximately 0.04M to selectively solubilize IgG. After mixing for about 15 minutes, pH of the suspension is adjusted to 5.2 with pH 4.0 acetate buffer. Cold alcohol (95%) is added to the suspension to a final concentration of 17%. During the alcohol addition the temperature of the suspension is lowered gradually to about −6° C. Three hundred and three grams of acid washed diatomaceous earth filter aid Celite® available from Celite Corporation is added as a filter aid to the suspension to a final concentration of about 2.0%. After mixing for one hour, the Celite and the Fraction III paste containing unwanted protein such as plasmin, plasminogen, IgA and IgM are then removed by filtration utilizing a filter press. The filtrate is further clarified by 0.45 μm and 0.2 μm filters. Thereafter the Fraction III supernatant is adjusted to pH 7.0 with 1.0M sodium bicarbonate, temperature is lowered to −7° C. while cold alcohol (95%) is added to a final concentration of 25%. The pH of the suspension if required, is adjusted to 7.2 and the precipitate, Fraction II is removed by filtration at −7° C.

Each kilogram of Fraction II paste is suspended in approximately 1.5 kg of cold aqueous solution maintained at 0 to 2° C. containing 0.2% albumin (human) and approximately 2.0% polyethylene glycol. pH is adjusted to 3.7±0.2 with dilute hydrochloric acid, after which the suspension is held at that pH while being mixed for 15 hours.

The pH of the solution is adjusted to 5.3 with dilute sodium hydroxide while maintaining the temperature at 0 to 2° C. and 50% polyethylene glycol (PEG) 3350 is added to the solution to give a final PEG concentration of 4%. The precipitate so formed is removed at 1° C. by filtration or centrifugation. The pH of the filtrate is adjusted to 4.9 with 1.0 N hydrochloric acid and bentonite is added to a final concentration of about 0.25%. The pH of the bentonite suspension is readjusted to about 5.2 and then the suspension is filtered or centrifuged at 1° C. to remove bentonite. The filtrate pH is adjusted to 8.0 with 0.25 N sodium hydroxide and 50% PEG 3350 solution is added to a final PEG concentration of 12%. The precipitate so formed (purified immune globulin) is removed at 0 to 2° C. by filtration or centrifugation.

The above sets forth a typical process usable for carrying out PEG fractionation. Other PEG fractionation processes are known in the art.

One hundred grams of PEG-purified immune globulin paste is suspended in 450 ml of cold water for injection. The pH of the suspension is adjusted to 5.5 by the addition of 5% acetic acid. After mixing the suspension for two hours at +5° C., 33.3 g of DEAE Sephadex® A-50 (Pharmacia) preequilibrated with 0.3% sodium chloride at pH 5.5 is added. After absorption for two hours, the DEAE resin is removed by filtration.

Tri-n-butyl phosphate (TNBP) and Polysorbate 80 mixture is added to the filtrate to yield a final concentration of 0.3% TNBP and 1.0 % Polysorbate 80. The solution is incubated overnight at +5° C. D-Sorbitol is then added to the treated solution to a final concentration of 33% and the stabilized IgG solution is mixed for one (1) hour, pH adjusted to 5.5 and heated overnight at 60° C.

The mixture is cooled to +5° C. and pH is adjusted to 5.8. To remove the solvent detergent, PEG and sorbitol, the mixture is treated with CM-Sephadex C-50 as follows: The solvent/detergent treated and heat treated solution is diluted fourfold with cold water. The diluted solution is split into three aliquotes. Sodium chloride is added to the aliquotes to yield a final concentration of 0.2%, 0.4% and 0.6% for suspensions a, b and c, respectively. Each aliquot is then treated with 0.65 g dry weight per gram of protein of CM-Sephadex® C-50 Pharmacia resin, pre-equilibrated at pH 5.8 and corresponding NaCl concentrations.

After the adsorption of the protein by the resin for 3±2 hours, the liquid is removed by filtration. The protein adsorbed resins are then washed with 0.2%, 0.4% and 0.6% sodium chloride solution, respectively, to remove residual polysorbate 80, TNBP, PEG and sorbitol. The washed protein adsorbed CM-Sephadex® C-50 (Pharmacia) resins are then resuspended in 1.5±0.5 N sodium chloride solution for 2±1 hours to desorb the adsorbed protein. The resins are separated from the desorbed protein solution by filtration.

As discussed herein, the 12% PEG stage and the anionic exchange resin treatment are optional steps. Further, a second PEG fractionation step can be employed instead of or in addition to cationic exchange resin treatment. Also, the heat treatment and solvent (solvent-detergent) viral inactivation steps can be carried out in any order.

Variations of the invention will be apparent to the skilled artisan.

We claim:

1. An intravenously-administrable γ-globulin solution produced by the process of preparing an intravenously administrable γ-globulin solution which comprises:

(a) subjecting an impure γ-globulin solution to polyethylene glycol fractionation for obtaining a purified γ-globulin;

(b) treating the polyethylene glycol purified solution of γ-globulin with an organic solvent for inactivating envelope viruses;

(c) heat treating the polyethylene glycol purified solution of γ-globulin under time and temperature conditions sufficient for inactivating heat sensitive viruses; and then (d) removing aggregates generated by the heat treatment;

wherein heat treatment step (c) is carried out on the γ-globulin-organic solvent solution resulting from step (b) without any intervening process.

2. An intravenously-administrable γ-globulin solution produced by the process of preparing an intravenously administrable γ-globulin solution which comprises:

(a) subjecting an impure γ-globulin solution to polyethylene glycol fractionation for obtaining a purified γ-globulin;

(b) treating the polyethylene glycol purified solution of γγ-globulin with an organic solvent for inactivating envelope viruses;

(c) heat treating the polyethylene glycol purified solution of γ-globulin under time and temperature conditions sufficient for inactivating heat sensitive viruses; and then (d) removing aggregates generated by the heat treatment;

wherein heat treatment step (c) is carried out on the γ-globulin-organic solvent solution resulting from step (b) without any intervening processing, and wherein an anionic exchange resin treatment is carried out prior to step (b) and a cationic exchange resin treatment is carried out after step (c).

* * * * *